May 9, 1972 R. G. JELLY Plant Pat. 3,166
YELLOW ROSE
Filed Oct. 24, 1969
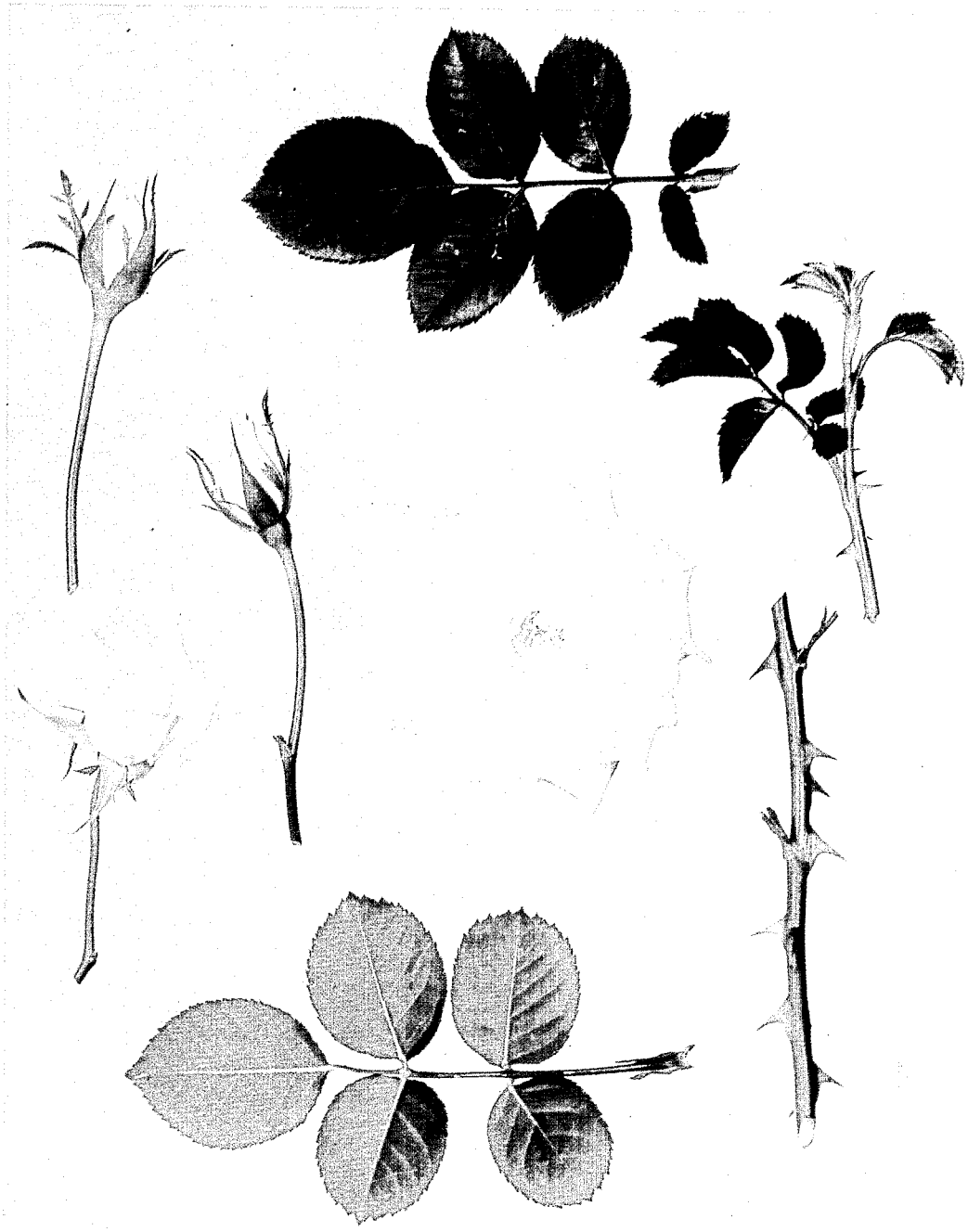
INVENTOR.
ROBERT G. JELLY
BY Rummler & Snow
Attys.

United States Patent Office

Plant Pat. 3,166
Patented May 9, 1972

3,166
YELLOW ROSE

Robert G. Jelly, Richmond, Ind., assignor to
E. G. Hill Co., Inc., Richmond, Ind.

Filed Oct. 24, 1969, Ser. No. 869,402
Int. Cl. A01h *5/00*
U.S. Cl. Plt.—24 1 Claim

ABSTRACT OF THE DISCLOSURE

A continuous and free blooming variety of floribunda rose plant for greenhouse culture, characterized by the very stable yellow color of its blooms, its vigorous and upright growth habit, and its improved winter productivity under low light intensities.

BACKGROUND OF THE INVENTION

My new variety of rose plant was developed by me at Richmond, Ind., with the object of improving on the color and growth habit of Golden Garnette (P.P. 1,898) and to produce a yellow rose plant having a more favorable winter productivity under commercial greenhouse conditions for cut flower production. The new rose plant originated as a seedling from a cross of Golden Garnette, as the seed parent, and an unnamed seedling, identified as 1–61YS in my breeding records, known to have a good winter productivity and vase life. Flowers produced, in greenhouse during February 1964, from a crossing made in October 1963, were observed to have the improved color characteristic desired and the plant was observed to have the upright growth habit, glossy foliage, and uniformity of cane that would make this variety a valuable addition to the greenhouse rose industry.

Successive asexual propagations of this new variety of rose plant by grafting under my direction at Richmond, Ind., and by budding at Livermore, Calif., have demonstrated that its distinguishing characteristics are fixed and hold true in every respect.

DESCRIPTION OF THE DRAWING

My new variety of rose plant is illustrated in the accompanying photographic drawing showing typical specimens of the bud, when the sepals first divide, half opened and fully opened blooms, specimens of the wood and young leaves, and specimens of a mature leaf showing upper and under surface characteristics.

DESCRIPTION OF THE NEW PLANT VARIETY

The following is a detailed description of my new variety of rose plant with color designations according to Robert S. Wilson's "Horticultural Colour Chart," Koster's "Color Guide," and Nickerson's "Color Fan," identified herein as (W), (K) and (N), respectively.

*The plant (greenhouse grown)*

Origin: Seedling (#25–64YS).

Parentage:

Seed parent.—Golden Garnette (P.P. 1,898).

Pollen parent.—An unnamed and unpatented seedling #1–61YS.

Classification: Floribunda. Type—Greenhouse use for cut flower production (tested negative for garden use).

Form: Bush.

Growth: Free and vigorous—habit—upright, much branched.

Foliage: Canes—Small to medium diameter.

*Main stems.*—Color—varying from moderate olive green 7.5GY4/4 (N) to spinach green 0960/1 (W). *Thorns*—several to many, hooked downward with long length and narrow base. Color—slightly lighter than dark orange yellow 10YR6/8 (N). *Prickles*—none. *Hairs*—none.

*Branches.*—Color—moderate yellow green 5GY5/6 (N). *Thorns*—several, hooked downward, medium length with long and narrow base. Color—strong greenish yellow 7.3Y6/7 (N). *Prickles*—none. *Hairs*—none.

Leaves: Abundant in quantity.

*Shape.*—Odd pinnate (compound).

*Size.*—Small to medium and moderately thick.

*Leaflets.*—3 to 7 in number. Shape—oval to slightly elliptical; apex, cuspidate; base, obtuse to acute; margin, irregularly serrate. Color—young upper surface—Fern Green 0862/2 (W) suffused with Ruby Red 827/1 (W). Young under surface—Sage Green, Plate 78 (K) suffused with Ruby Red 827/1 (W) (charted just as can shows buds). Mature upper surface—Ivy Green 000/060/2 (W). Mature under surface—Sage Green, Plate 78 (K). Texture—leathery. Appearance—glossy.

*Rachis.*—Upper side—light to medium grooved and prickly—under side—thorny.

*Stipules.*—Medium length and medium width, with points of medium length, turning out at an angle of less than 45 degrees.

*The bud*

Size: Medium small, before calyx breaks and when first petals open.

Form: Before calyx breaks—short pointed, without a conspicuous neck, with foliaceous appendages on the bud surface and with slender, bristle-like foliaceous parts extending beyond the top of the bud for one-half or more of the bud length.

Color: Calyx—Scheeles Green 860/3 (W). As calyx breaks; outside color—Canary Yellow 2 (W). As first petal opens; outside—Buttercup Yellow 5/1 (W); inside—shaded from Aureolin 3/1 (W) to Buttercup Yellow 5/1 (W).

Sepals: Permanent and of medium length. Color—Inside—shaded from Lavender Green 000761 (W) to Pea Green 61/2 (W). Outside—shaded from Spinach Green, Plate 76 (K) to Sap Green 62/2 (W).

Opening in greenhouse: Bud opens well. It is affected by hot weater in that there is a slight decrease in bud size.

Peduncle: Short length, small to medium diameter, strong and erect.

Bark.—Smooth.

Color.—Fern Green 0862/1 (W). No thorns, prickles or hairs.

*The Flower*

Blooming habit: Continuous and free (in greenhouse).

Size: Medium small, when fully opened, 3 to 3½ inches in diameter.

Borne: One to several to a stem, disbudded commercially to one.

Shape: High centered at first, becoming flat to high centered, petals at first remaining very tightly rolled outward. At maturity, petals become very loosely rolled outward.

Petalage: Double (but the stamens are not hidden). 32 to 38 petals arranged regularly.

*Shape.*—Outside—oval to slightly obvate, apex generally entire. Intermediate—obvate, apex mucronate with one defined notch. Inside—obvate, apex entire with a slightly cuspidate tip.

*Color.*—Colors may be modified by being shaded with other colors.

The following is from a newly opened flower grown in greenhouse in April 1969 at Richmond, Ind.:

*Outside petal.*—Outer surface—Aureolin 3/1 (W), with occasional petal shading, to Aureolin 3/3 (W); inside surface—Aureolin 3/1 (W), with occasional shading at petal tip to Aureolin 3/3 (W).

*Intermediate petal.*—Outside surface, shaded from Aureolin 3/2 (W) at petal edge to Aureolin 3/1 (W); inside surface—shaded from Aureolin 3/2 (W) at petal edge to Aureolin 3/1 (W).

*Inner petal.*—Outside surface—shaded from Aureolin 3/1 (W) to Aureolin 3 (W) at petal base; inside surface—shaded from Aureolin 3/2 (W) at petal edge to Aureolin 3 (W) at petal base.

The following is from a rose opened for three days in greenhouse in April 1969 at Richmond, Ind.:

*Outside petal.*—Outer surface—shaded from Dresden Yellow 64/3 (W) to Aureolin 3 (W) at petal base; inside surface—shaded from Canary Yellow 2/3 (W) to Aureolin 3 (W) at petal base.

*Intermediate petal.*—Outer surface — shaded from Canary Yellow 2/2 (W) to Canary Yellow 2 (W) at petal base; inside surface—shaded from Mimosa Yellow 602/1 (W) to Canary Yellow 2 (W) at petal base.

*Inner petal.*—Outer surface—shaded from Mimosa Yellow 602/1 (W) to Canary Yellow 2/1 (W) at petal base.

General color effect:

*Newly opened flower.*—Aureolin 3/1 (W).

*Three days opened flower.*—Aureolin 3/2 (W).

Texture: Moderately thin and soft.

Appearance: Satiny, inside and outside.

Stem: Medium strong, short to medium length.

Fragrance: Moderate—sweetbriar.

Persistence: In greenhouse, petals persist.

Effect of hot, dry weather: Slight decrease in flower color intensity, fading to Aureolin 3/2 (W).

Lasting quality: Cut flowers grown in greenhouse kept at living room temperatures—seven days in February.

*Reproductive organs*

Stamens: Medium number tucked in calyx and arranged regularly about the pistils.

*Anthers.*—Small. All open at once. Color—Canary Yellow 2/2 (W) with Moderate Reddish Brown 7.5R3/6 (N) edge.

*Filaments.* — Medium length. Most with anthers. Color—Aureolin 3 (W).

*Pollen.*—Moderate. Color—Slightly lighter than Strong Orange 5YR6/11 (N).

Pistils: Medium number.

*Styles.*—Fairly even, medium length, moderately thin and bunched. Color—Sulphur Yellow 1/3 (W) at base and Strong Red 5R4/12 (N) toward style tip.

*Stigmas.*—Color: Empire Yellow 603 (W).

This new variety of yellow rose plant is a distinct improvement over its seed parent Golden Garnette (P.P. 1,898) in many respects. The growth of the new variety is more erect and the foliage has more gloss and eye appeal. The yellow color of the bloom is more stable than Golden Garnette with much less fading and variation; and the excellent color, texture and vase life of the blooms of the new variety, together with its uniformity of cane and better performance under the low light intensities of winter, make it a valuable addition for the greenhouse rose industry.

I claim:

1. A new and distinct variety of rose plant substantially as herein shown and described, characterized by its continuous and free blooming production of Aureolin Yellow flowers under greenhouse culture, its improved winter-time productivity, its more vigorous and erect growth habit, and the more stable color and longer vase life of the cut flowers.

No references cited.

ROBERT E. BAGWILL, Primary Examiner